United States Patent
Armel et al.

(10) Patent No.: US 10,477,863 B2
(45) Date of Patent: Nov. 19, 2019

(54) USE OF HERBICIDAL COMPOSITIONS FOR CONTROLLING UNWANTED VEGETATION

(71) Applicant: BASF SE, Ludwigshafen am Rheim (DE)

(72) Inventors: Gregory Armel, Clayton, NC (US);
Rex A. Liebl, Raleigh, NC (US);
Steven Joseph Bowe, Apex, NC (US);
Glenn W. Oliver, Apex, NC (US)

(73) Assignee: BASF SE, Ludwigshafen am Rhein (DE)

( * ) Notice: Subject to any disclaimer, the term of this patent is extended or adjusted under 35 U.S.C. 154(b) by 8 days.

(21) Appl. No.: 15/750,414

(22) PCT Filed: Aug. 3, 2016

(86) PCT No.: PCT/EP2016/068492
§ 371 (c)(1),
(2) Date: Feb. 5, 2018

(87) PCT Pub. No.: WO2017/021430
PCT Pub. Date: Feb. 9, 2017

(65) Prior Publication Data
US 2018/0242580 A1 Aug. 30, 2018

Related U.S. Application Data

(60) Provisional application No. 62/201,626, filed on Aug. 6, 2015.

(51) Int. Cl.
*A01N 37/40* (2006.01)
*A01N 39/04* (2006.01)
*A01N 37/10* (2006.01)
*A01N 39/02* (2006.01)

(52) U.S. Cl.
CPC ............ *A01N 37/40* (2013.01); *A01N 37/10* (2013.01); *A01N 39/02* (2013.01); *A01N 39/04* (2013.01); *A01N 2300/00* (2013.01)

(58) Field of Classification Search
CPC ........ A01N 37/40; A01N 37/10; A01N 39/02; A01N 39/04; A01N 2300/00
See application file for complete search history.

(56) References Cited

U.S. PATENT DOCUMENTS

| | | |
|---|---|---|
| 8,648,012 B2 | 2/2014 | Patzoldt et al. |
| 8,709,978 B2 | 4/2014 | Estrine et al. |
| 2015/0105254 A1 | 4/2015 | Li |

FOREIGN PATENT DOCUMENTS

| | | | |
|---|---|---|---|
| EP | 2554049 B1 | 3/2016 | |
| GB | 2190293 A1 | 11/1987 | |
| WO | 10086437 A2 | 8/2010 | |
| WO | WO-2010086437 A2 * | 8/2010 | ............ A01N 37/30 |
| WO | 13189773 A1 | 12/2013 | |

OTHER PUBLICATIONS

Nufarm, MSDS for Jepolinex, 2012. (Year: 2012).*
Benkov et al., "Effect of Some Herbicides on Cypress Spurge (*Euphorbia cyparissias*) Occurring in Natural Pastures," Database CA [online] Chemical Abstracts Service, Columbus, Ohio, US; XP002746560, retrieved from STN Database accession No. 1974:56380, May 12, 1984.
Benkov et al., "Effect of Herbicides on Dandelion (*Taraxacum othcinalis*) in City Lawns," Database CAPLUS [Online], XP002746559, retrieved from CAPLUS, STN Database accession No. 1972-401683, Jan. 1, 1971.
International Search Report, issued in PCT/EP2016/068492, dated Sep. 14, 2016.
Search Report, issued in EP Application No. 15183127.8, dated Oct. 15, 2015.
International Preliminary Report on Patentability, issued in PCT/EP2016/068492, dated Feb. 6, 2018.

* cited by examiner

*Primary Examiner* — John Pak
*Assistant Examiner* — Nathan W Schlientz
(74) *Attorney, Agent, or Firm* — Brinks Gilson & Lione

(57) ABSTRACT

The present invention relates to the use of a herbicidal composition comprising as component A) 4-(2,4-dichlorophenoxy)butanoic acid or salts or esters thereof and as component B) 3,6-dichloro-2-methoxybenzoic acid or salts or esters thereof for controlling unwanted vegetation in crop plants. The present invention also relates to a method for controlling unwanted vegetation in crop plants, which comprises allowing a composition comprising said components A) and B) to act on plants, their seeds and/or their habitat.

19 Claims, No Drawings

USE OF HERBICIDAL COMPOSITIONS FOR CONTROLLING UNWANTED VEGETATION

This application is a National Stage application of International Application No. PCT/EP2016/068492, filed Aug. 3, 2016, which claims the benefit of U.S. Provisional Application No. 62/201,626, filed Aug. 6, 2015.

The present invention relates to the use of a herbicidal composition comprising as component A) 4-(2,4-dichlorophenoxy)butanoic acid or salts or esters thereof and as component B) 3,6-dichloro-2-methoxybenzoic acid or salts or esters thereof for controlling unwanted vegetation in crop plants. The present invention also relates to a method for controlling unwanted vegetation in crop plants, which comprises allowing a composition comprising said components A) and B) to act on plants, their seeds and/or their habitat.

In the case of crop protection compositions, it is desirable to increase the specific activity of an active compound and the reliability of the effect. It is particularly desirable for the crop protection composition to control the harmful plants effectively, but at the same time to be compatible with the useful plants in question. Also desirable is a broad spectrum of activity allowing the simultaneous control of a variety of harmful plants. Frequently, this cannot be achieved using a single herbicidally active compound.

With many highly effective herbicides, there is the problem that their compatibility with useful plants, in particular dicotyledonous crop plants, such as soybean, cotton, oilseed rape and graminaceous plants, such as barley, millet, corn, rice, wheat and sugar cane, is not always satisfactory, i.e. in addition to the harmful plants, the crop plants, too, are damaged on a scale which cannot be tolerated. By reducing the application rates, the useful plants are spared; however, naturally, the extent of the control of harmful plants decreases too.

It is known that special combinations of different specifically active herbicides may result in enhanced activity of an herbicide component in the sense of an over additive effect. In this manner, it may be feasible to reduce the application rates of herbicidally active compounds required for controlling the harmful plants.

Frequently, it is a problem that herbicides can only be applied within a narrow time frame in order to achieve the desired herbicidal action, which time frame may be unpredictably influenced by weather conditions.

Furthermore, it is known that in some cases joint application of specifically acting herbicides with organic active compounds, some of which may also have herbicidal activity, provides better crop plant compatibility. In these cases, the active compounds act as antidotes or antagonists and are also referred to as safeners, since they reduce or even prevent damage of herbicides to the crop plants.

4-(2,4-Dichlorophenoxy)butanoic acid of formula (I), or component A), is commonly known as 2,4-DB (CAS 94-82-6). 3,6-Dichloro-2-methoxybenzoic acid of formula (II), or component B), is commonly known as dicamba (CAS 1918-00-9). Both, components A) and B), or their salts or esters, have been described for use as herbicides (The Compendium of Pesticide Common Names (http://www.alanwood.net/pesticides/); Farm Chemicals Handbook 2000 volume 86, Meister Publishing Company, 2000; B. Fock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998).

The combination of 4-(2,4-dichlorophenoxy)butanoic acid and 3,6-dichloro-2-methoxybenzoic acid was described in Chemical Abstract (CAS 8067-64-9) and was entered on Nov. 16, 1984.

U.S. Pat. No. 8,648,012 describes herbicidal compositions comprising naptalam and methods for the control of unwanted vegetation with compositions comprising naptalam and dicamba, which may further comprise 4-(2,4-dichlorophenoxy)butanoic acid or salts or esters thereof. U.S. Pat. No. 8,709,978 describes herbicide compositions containing at least one herbicide from the family of phenoxyalkanoic acids in acid form and/or a benzoic acid derivative, and at least one solvent or oil, characterized in that the composition includes at least one surfactant and contains from 0 to 5% by mass of water.

US 20150105254 discloses aqueous based pesticide compositions having a high concentration of a water-soluble salt of a herbicide and a waterinsoluble pesticide, which are stable upon storage in various thermal environments, and upon dilution in water form a stable emulsion.

It is an object of the present invention to provide the use of herbicidal compositions which are highly active against unwanted harmful plants, showing enhanced activity in the sense of an over additive effect. At the same time, the compositions should have good compatibility with useful plants. In addition, the compositions according to the invention should have a broad spectrum of activity. These and further objects are achieved by the use of the herbicidal composition below.

Accordingly, the present invention relates to the use of herbicidal compositions comprising as component
A) 4-(2,4-dichlorophenoxy)butanoic acid of formula (I) or salts or esters thereof

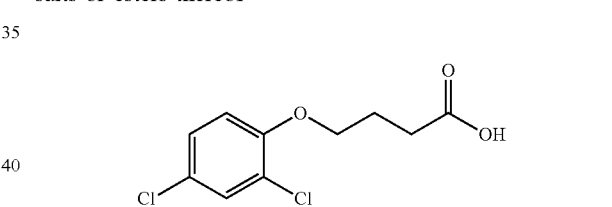

and as component
B) 3,6-dichloro-2-methoxybenzoic acid of formula (II) or salts or esters thereof

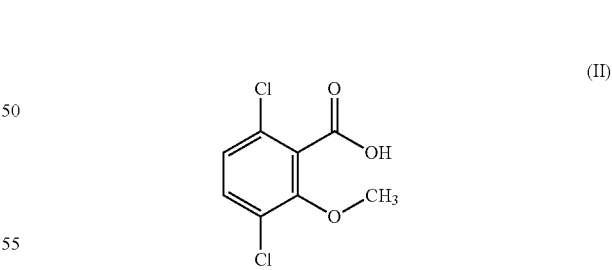

wherein the weight ratio of components A) to B) based on acid equivalents is from 1:12 to 1:100, for controlling unwanted vegetation in crop plants.

Surprisingly, the use of herbicidal compositions according to the invention comprising component A) and component B), achieve better herbicidal activity, i.e. better activity against harmful plants, than would have been expected based on the herbicidal activity observed for the individual compounds, or a broader activity spectrum. If the herbicidal activity observed exceeds the expected additive activity of the individual compounds, an over additive effect is present. Moreover, the time frame, within which the desired herbicidal action can be achieved, may be expanded by the use of compositions according to the invention comprising component A) and component B). This allows a more flexibly timed application of the compositions according to the present invention in comparison with the single compounds.

In one aspect the present invention relates to the use of an aqueous herbicidal composition comprising as component A) a salt of 4-(2,4-dichlorophenoxy)butanoic acid and as component B) a salt of 3,6-dichloro-2-methoxybenzoic acid for controlling unwanted vegetation in crop plants.

In another aspect the present invention relates to the use of an aqueous herbicidal composition essentially consisting of as component A) a salt of 4-(2,4-dichlorophenoxy)butanoic acid and as component B) a salt of 3,6-dichloro-2-methoxybenzoic acid for controlling unwanted vegetation in crop plants.

The invention furthermore relates to a method for controlling unwanted vegetation, in particular in fields where crop plants are cultivated which comprises allowing a composition comprising said components A) and B) to act on plants, their seeds and/or their habitat.

As used herein, the term "crop plant" is to be construed as the plant to be cultivated in a field. As used herein, the terms "undesirable vegetation" and "harmful plants" are synonyms and relate to plants which are commonly known as weeds.

If the component A) or the component B) or, optionally, further pesticides C as described herein, or their salts or esters respectively, are capable of forming geometrical isomers, for example E/Z stereoisomers with regard to a double bond, it is possible to use both, the pure isomers and mixtures thereof, in the compositions according to the invention.

If the component A) or the component B) or further pesticides C as described herein, or their salts or esters respectively, have one or more centers of chirality and, as a consequence, are present as enantiomers or diastereomers, it is possible to use both, the pure enantiomers and diastereomers and their mixtures, in the compositions according to the invention.

The term "salt" refers to chemical compounds, which comprise an anion and a cation. The carboxylic acids of compounds of the formula (I) or (II) carry ionizable carboxylic acid groups to form the corresponding carboxylate anions. They can thus be employed in the form or their salts. The ratio of anions to cations usually depends on the electric charge of the ions. Typically, salts dissociate when dissolved in water in anions and cations.

Suitable cations are the ions of the alkali metals, preferably of lithium, sodium and potassium, of the alkaline earth metals, preferably of calcium and magnesium, and of the transition metals, preferably of manganese, copper, zinc and iron, further ammonium and substituted ammonium in which one to four hydrogen atoms are replaced by $C_1$-$C_4$-alkyl, hydroxy-$C_1$-$C_4$-alkyl, $C_1$-$C_4$-alkoxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, heptylammonium, dodecylammonium, tetradecylammonium, tetramethylammonium, tetraethylammonium, tetrabutylammonium, 2-hydroxyethylammonium (olamine salt), 2-(2-hydroxyeth-1-oxy)eth-1-ylammonium (diglycolamine salt), di(2-hydroxyeth-1-yl)ammonium (diolamine salt), tris(2-hydroxyethyl)ammonium (trolamine salt), tris(2-hydroxypropyl)ammonium, benzyltrimethylammonium, benzyltriethylammonium, N,N,N-trimethylethanolammonium (choline salt), furthermore phosphonium ions, sulfonium ions, preferably tri($C_1$-$C_4$-alkyl)sulfonium, such as trimethylsulfonium, and sulfoxonium ions, preferably tri($C_1$-$C_4$-alkyl)sulfoxonium, and finally the salts of polybasic amines such as N,N-bis-(3-aminopropyl)methylamine and diethylenetriamine.

In one embodiment, the present invention relates to the use of herbicidal compositions comprising component A) and/or component B) as a salt, wherein the cation is independently selected from any of the suitable cations mentioned herein and a cationic polyamine (B) of the formula (B1)

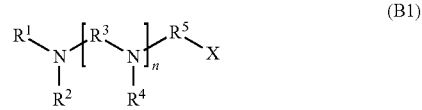

wherein $R^1$, $R^2$, $R^4$, $R^6$ and $R^7$ are independently H or $C_1$-$C_6$-alkyl, which is optionally substituted with OH,
$R^3$ and $R^5$ are independently $C_2$-$C_4$-alkylene,
X is OH or $NR^6R^7$, and
n is from 1 to 20;
or of the formula (B2)

wherein $R^{10}$ and $R^{11}$ are independently H or $C_1$-$C_6$-alkyl,
$R^{12}$ is $C_1$-$C_{12}$-alkylene, and
$R^{13}$ is an aliphatic $C_5$-$C_8$ ring system, which comprises either nitrogen in the ring or which is substituted with at least one unit $NR^{10}R^{11}$.

Cationic polyamines (B) of the formula (B1) and (B2) were described in WO 2011/039172. The term "polyamine" within the meaning of the invention relates to an organic compound comprising at least two amino groups, such as an primary, secondary or tertiary amino group.

The term "cationic polyamine" refers to a polyamine, which is present as cation. Preferably, in a cationic polyamine at least one amino group is present in the cationic form of an ammonium, such as R—N$^+$H$_3$, R$_2$—N$^+$H$_2$, or R$_3$—N$^+$H. When formulae, such as (B1), (B2), (B3) or (B4), show neutral molecules, they usually refer to their cationic form (i.e. at least one amino group is present in the cationic form of an ammonium, such as R—N$^+$H$_3$, R$_2$—N$^+$H$_2$, or R$_3$—N$^+$H). For example, the cationic form of B1.1 may be represented by at least one of the following formulae:

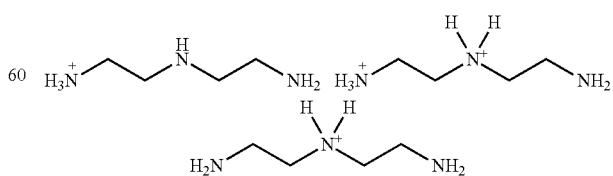

For example, the cationic form of B1.2 may be represented by at least one of the following formulae:

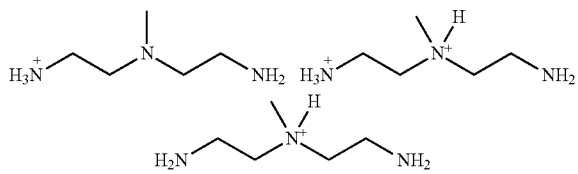

For example, the cationic form of B1.6 may be represented by at least one of the following formulae:

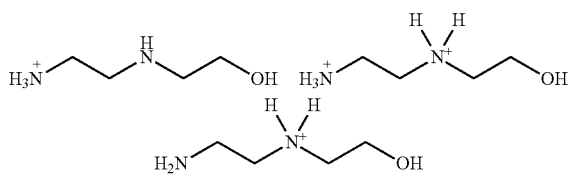

An expert is aware which of the amine groups in the cationic polyamine is preferably protonated, because this depends for example on the pH or the physical form. In aqueous solutions the alkalinity of the amino groups of the cationic polyamine increases usually from tertiary amine to primary amine to secondary amine.

In one embodiment the cationic polyamine has the formula

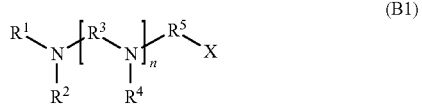
(B1)

wherein $R^1$, $R^2$, $R^4$, $R^6$, $R^7$ are independently H or $C_1$-$C_6$-alkyl, which is optionally substituted with OH, $R^3$ and $R^5$ are independently $C_2$-$C_{10}$-alkylene, X is OH or $NR^6R^7$, and n is from 1 to 20. $R^1$, $R^2$, $R^4$, $R^6$ and $R^7$ are independently H or methyl. In one aspect $R^1$, $R^2$, $R^6$ and $R^7$ are H. In another aspect $R^6$ and $R^7$ are identical to $R^1$ and $R^2$, respectively. In one embodiment $R^3$ and $R^5$ are independently $C_2$-$C_3$-alkylene, such as ethylene (—$CH_2CH_2$—), or n-propylene (—$CH_2CH_2CH_2$—). Typically, $R^3$ and $R^5$ are identical. $R^3$ and $R^5$ may be linear or branched, unsubstituted or substituted with halogen. In one aspect $R^3$ and $R^5$ are linear. In another aspect $R^3$ and $R^5$ are unsubstituted. According to one aspect X is $NR^6R^7$. In one embodiment n is from 1 to 10, or from 1 to 6, or from 1 to 4. In another embodiment, n is from 2 to 10. According to one aspect $R^1$, $R^2$, and $R^4$ are independently H or methyl, $R^3$ and $R^5$ are independently $C_2$-$C_3$-alkylene, X is OH or $NR^6R^7$, and n is from 1 to 10.

In cationic polyamines of the formula (B1) the group X is bound to $R^5$, which is a $C_2$-$C_{10}$-alkylene group. This means that X may be bound to any carbon atom of the $C_2$-$C_{10}$-alkylene group. Examples of a unit —$R^5$—X are —$CH_2$—$CH_2$—$CH_2$—OH or —$CH_2$—CH(OH)—$CH_3$.

In one aspect of the invention $R^1$, $R^2$, $R^4$, $R^6$, $R^7$ in cationic polyamines of the formula (B1) are independently H or $C_1$-$C_6$-alkyl, which is optionally substituted with OH. An example of such a substitution is formula (B1.9), in which $R^4$ is H or $C_1$-$C_6$-alkyl substituted with OH (more specifically, $R^4$ is $C_3$-alkyl substituted with OH. Preferably, $R^1$, $R^2$, $R^4$, $R^6$, $R^7$ are independently H or $C_1$-$C_6$-alkyl.

In another embodiment the cationic polymer of the formula (B1) is free of ether groups (—O—). Ether groups are known to enhance photochemical degradation resulting in explosive radicals or peroxy groups.

Examples for cationic polyamines of the formula (B1) wherein X is $NR^6R^7$ are diethylenetriamine (DETA, (B4) with k=1, corresponding to (B1.1)), triethylenetetraamine (TETA, (B4) with k=2), tetraethylenepentaamine (TEPA, (B4) with k=3). Technical qualities of TETA are often mixtures comprising in addition to linear TETA as main component also tris-aminoethylamine TAEA, Piperazino-ethylethylenediamine PEEDA and Diaminoethylpiperazine DAEP. Technical qualities of TEPA a are often mixtures comprising in addition to linear TEPA as main component also aminoethyltris-aminoethylamine AE-TAEA, aminoethyldiaminoethylpiperazine AE-DAEP and aminoethylpiperazinoethylethylenediamine AE-PEEDA. Such ethyleneamines are commercially available from Dow Chemical Company. Further examples are Pentamethyldiethylenetriamine PM DETA (B1.3), N,N,N',N",N"-pentamethyl-dipropylenetriamine (B1.4) (commercially available as Jeffcat® ZR-40), N,N-bis(3-dimethylaminopropyl)-N-isopropanolamine (commercially available as Jeffcat® ZR-50), N'-(3-(dimethylamino)propyl)-N,N-dimethyl-1,3-propanediamine (B1.5) (commercially available as Jeffcat® Z-130), and N,N-Bis(3-aminopropyl)methylamine BAPMA (B1.2). Especially preferred are (B4), wherein k is from 1 to 10, (B1.2), (B1.4) and (B1.5). Most preferred are (B4), wherein k is 1, 2, 3, or 4 and (B1.2). In particular preferred are (B1.1) and (B1.2).

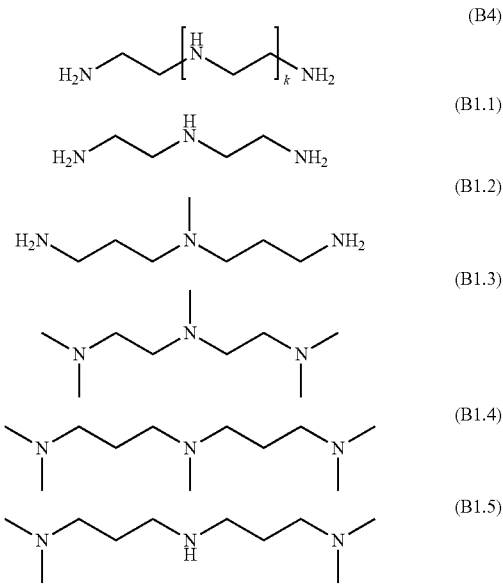

Examples for polyamines of the formula (B1) wherein X is OH are N-(3-dimethylaminopropyl)-N,N-diisopropanolamine DPA (B1.9), N,N,N'-trimethylaminoethyl-ethanolamine (B1.7) (commercially available as Jeffcat® Z-110), aminopropylmonomethylethanolamine APMMEA (B1.8), and aminoethylethanolamine AEEA (B1.6).

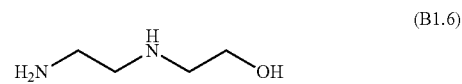

(B1.7)
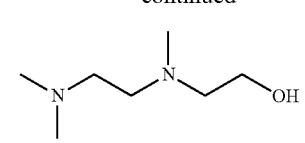

(B1.8)
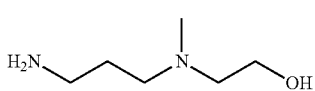

(B1.9)
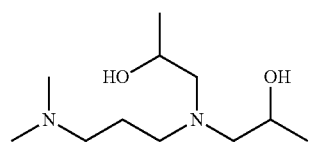

In another embodiment the cationic polyamine has the formula (B2)
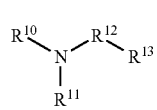

wherein $R^{10}$ and $R^{11}$ are independently H or $C_1$-$C_6$-alkyl, $R^{12}$ is $C_2$-$C_{12}$-alkylene, and $R^{13}$ is an aliphatic $C_5$-$C_8$ ring system, which comprises either nitrogen in the ring or which is substituted with at least one unit $NR^{10}R^{11}$.

In one embodiment $R^{10}$ and $R^{11}$ in cationic polyamines of the formula (B2) are independently H or methyl, more preferably H. Typically $R^{10}$ and $R^{11}$ are linear or branched, unsubstituted or substituted with halogen. Preferably, $R^{10}$ and $R^{11}$ are unsubstituted and linear. More preferably, $R^{10}$ and $R^{11}$ are identical.

In one aspect of the invention $R^{12}$ in cationic polyamines of the formula (B2) is $C_2$-$C_4$-alkylene, such as ethylene (—$CH_2CH_2$—), or n-propylene (—$CH_2CH_2CH_2$—). $R^{12}$ in cationic polyamines of the formula (B2) may be linear or branched, preferably it is linear. $R^{12}$ in cationic polyamines of the formula (B2) may be unsubstituted or substituted with halogen, preferably it is unsubstituted.

In one aspect of the invention $R^{13}$ in cationic polyamines of the formula (B2) is an aliphatic $C_5$-$C_8$ ring system, which comprises either nitrogen in the ring or which is substituted with at least one unit $NR^{10}R^{11}$. Preferably, $R^{13}$ is an aliphatic $C_5$-$C_8$ ring system, which comprises nitrogen in the ring. The $C_5$-$C_8$ ring system may be unsubstituted or substituted with at least one $C_1$-$C_6$ alkyl group or at least one halogen. Preferably, the $C_5$-$C_8$ ring system is unsubstituted or substituted with at least one $C_1$-$C_4$ alkyl group. Examples for an aliphatic $C_5$-$C_8$ ring system, which comprises nitrogen in the ring, are piperazyl groups. Examples for $R^{13}$ being an aliphatic $C_5$-$C_8$ ring system, which comprises nitrogen in the ring, are the compounds of the formulat (B2.11) and (B2.12) below. Examples for $R^{13}$ being an aliphatic $C_5$-$C_8$ ring system, which is substituted with at least one unit $NR^{10}R^{11}$ is the compound of the formula (B2.10) below.

In another aspect of the invention $R^{10}$ and $R^{11}$ in cationic polyamines of the formula (B2) are independently H or methyl, $R^{12}$ is $C_2$-$C_3$-alkylene, and $R^{13}$ is an aliphatic $C_5$-$C_8$ ring system, which comprises oxygen or nitrogen in the ring. In another preferred embodiment the cationic polymer of the formula (B2) is free of ether groups (—O—).

Suitable cationic polyamines of formula (B2) are isophorone diamine ISPA (B2.10), aminoethylpiperazine AEP (B2.11), and 1-methyl-4-(2-dimethylaminoethyl)piperazine TAP (B2.12). These compounds are commercially available from Huntsman or Dow, USA. Preferred are (B2.10) and (B2.11), more preferably (B2.11). In another embodiment (B2.11) and (B2.12) are preferred.

(B2.10)
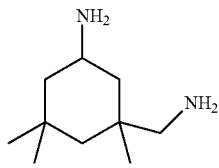

(B2.11)
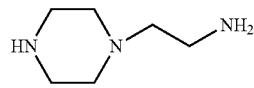

(B2.12)
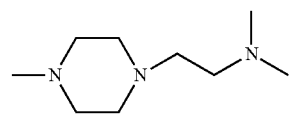

Other suitable salts of component A) include 2,4-DB-sodium, 2,4-DB-potassium, 2,4-DB-dimethylammonium and 2,4-DB-N,N-bis-(3-aminopropyl)methylamine, particularly preferred is 2,4-DB-N,N-bis-(3-aminopropyl)methylamine. Suitable esters of 2,4-DB are, for example, 2,4-DB-butyl and 2,4-DB-isoctyl.

Other suitable salts of component B), include dicamba-sodium, dicamba-potassium, dicamba-methylammonium, dicamba-dimethylammonium, dicamba-isopropylammonium, dicamba-diglycolamine, dicamba-olamine, dicamba-diolamine, dicamba-trolamine, dicamba-N,N-bis-(3-aminopropyl)methylamine and dicamba-diethylenetriamine; particularly preferred is dicamba-N,N-bis-(3-aminopropyl)methylamine. Examples of a suitable ester are dicamba-methyl and dicamba-butotyl (construed as 2-butoxyethyl).

According to one aspect of the invention both components A) and B) of the herbicidal composition are present in the form of their salts; particularly both components A) and B) are present in the form of their salts and have the same cation; most particularly components A) and B) both form a salt with N,N-bis-(3-aminopropyl)methylamine salt or diethylenetriamine.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

According to one aspect of the invention, the composition according to the invention comprises component A) and component B) and at least one, preferably exactly one further pesticide C. Examples of pesticides C which can be used in combination with the composition comprising component A) and component B) according to the present invention are selected from the groups b1) to b15) and from safeners as exemplified herein below:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim, tralkoxydim, 4-(4'-Chloro-4-cyclopropyl-2'-fluoro[1,1'-biphenyl]-3-yl)-5-hydroxy-2,2,6,6-tetramethyl-2H-pyran-3(6H)-one (CAS 1312337-72-6); 4-(2',4'-Dichloro-4-cyclopropyl[1,1'-biphenyl]-3-yl)-5-hydroxy-2,2,6,6-tetramethyl-2H-pyran-3(6H)-one (CAS 1312337-45-3); 4-(4'-Chloro-4-ethyl-2'-fluoro[1,1'-biphenyl]-3-yl)-5-hydroxy-2,2,6,6-tetramethyl-2H-pyran-3(6H)-one (CAS 1033757-93-5); 4-(2',4'-Dichloro-4-ethyl[1,1'-biphenyl]-3-yl)-2,2,6,6-tetramethyl-2H-pyran-3,5(4H,6H)-dione (CAS 1312340-84-3); 5-(Acetyloxy)-4-(4'-chloro-4-cyclopropyl-2'-fluoro[1,1'-biphenyl]-3-yl)-3,6-dihydro-2,2,6,6-tetramethyl-2H-pyran-3-one (CAS 1312337-48-6); 5-(Acetyloxy)-4-(2',4'-dichloro-4-cyclopropyl-[1,1'-biphenyl]-3-yl)-3,6-dihydro-2,2,6,6-tetramethyl-2H-pyran-3-one; 5-(Acetyloxy)-4-(4'-chloro-4-ethyl-2'-fluoro[1,1'-biphenyl]-3-yl)-3,6-dihydro-2,2,6,6-tetramethyl-2H-pyran-3-one (CAS 1312340-82-1); 5-(Acetyloxy)-4-(2',4'-dichloro-4-ethyl[1,1'-biphenyl]-3-yl)-3,6-dihydro-2,2,6,6-tetramethyl-2H-pyran-3-one (CAS 1033760-55-2); 4-(4'-Chloro-4-cyclopropyl-2'-fluoro[1,1'-biphenyl]-3-yl)-5,6-dihydro-2,2,6,6-tetramethyl-5-oxo-2H-pyran-3-yl carbonic acid methyl ester (CAS 1312337-51-1); 4-(2',4'-Dichloro-4-cyclopropyl-[1,1'-biphenyl]-3-yl)-5,6-dihydro-2,2,6,6-tetramethyl-5-oxo-2H-pyran-3-yl carbonic acid methyl ester; 4-(4'-Chloro-4-ethyl-2'-fluoro[1,1'-biphenyl]-3-yl)-5,6-dihydro-2,2,6,6-tetramethyl-5-oxo-2H-pyran-3-yl carbonic acid methyl ester (CAS 1312340-83-2); 4-(2',4'-Dichloro-4-ethyl[1,1'-biphenyl]-3-yl)-5,6-dihydro-2,2,6,6-tetramethyl-5-oxo-2H-pyran-3-yl carbonic acid methyl ester (CAS 1033760-58-5); and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:

sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuron-methyl, imazosulfuron, iodosulfuron, iodosulfuron-methyl-sodium, iofensulfuron, iofensulfuron-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8), sulfonylaminocarbonyl-triazolinone herbicides such as flucarbazone, flucarbazone-sodium, propoxycarbazone, propoxycarbazone-sodium, thiencarbazone and thiencarbazone-methyl; and triafamone;

among these, a preferred embodiment of the invention relates to those compositions comprising at least one imidazolinone herbicide;

b3) from the group of the photosynthesis inhibitors:

amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:

acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, tiafenacil, trifludimoxazin, ethyl [3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100, N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethyl-phenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 452100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 2-(2,2,7-trifluoro-3-oxo-4-prop-2-ynyl-3,4-dihydro-2H-benzo[1,4]oxazin-6-yl)-4,5,6,7-tetrahydro-isoindole-1,3-dione (CAS 1300118-96-0, 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione (CAS 1304113-05-0), methyl (E)-4-[2-chloro-5-[4-chloro-5-(difluoromethoxy)-1H-methyl-pyrazol-3-yl]-4-fluoro-phenoxy]-3-methoxy-but-2-enoate [CAS 948893-00-3], and 3-[7-Chloro-5-fluoro-2-(trifluoromethyl)-1H-benzimidazol-4-yl]-1-methyl-6-(trifluoromethyl)-1H-pyrimidine-2,4-dione (CAS 212754-02-4);

b5) from the group of the bleacher herbicides:
PDS inhibitors: beflubutamid, diflufenican, fluridone, flurochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, bicyclopyrone, clomazone, fenquinotrione, isoxaflutole, mesotrione, pyrasulfotole, pyrazolynate, pyrazoxyfen, sulcotrione, tefuryltrione, tembotrione, tolpyralate, topramezone, bleacher, unknown target: aclonifen, amitrole and flumeturon;

b6) from the group of the EPSP synthase inhibitors:
glyphosate, glyphosate-isopropylammonium, glyposate-potassium and glyphosate-trimesium (sulfosate);

b7) from the group of the glutamine synthase inhibitors:
bilanaphos (bialaphos), bilanaphos-sodium, glufosinate, glufosinate-P and glufosinate-ammonium;

b8) from the group of the DHP synthase inhibitors:
asulam;

b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: carbetamide, chlorpropham, flamprop, flamprop-isopropyl, flamprop-methyl, flamprop-M-isopropyl and propham, among these, compounds of group K1, in particular dinitroanilines are preferred;

b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide, napropamide and napropamide-M, tetrazolinones such fentrazamide, and other herbicides such as anilofos, cafenstrole, fenoxasulfone, ipfencarbazone, piperophos, pyroxasulfone and isoxazoline compounds of the formulae II.1, II.2, II.3, II.4, II.5, II.6, II.7, II.8 and II.9

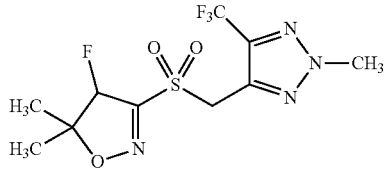

II.3

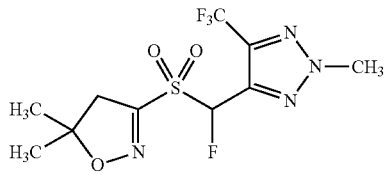

II.4

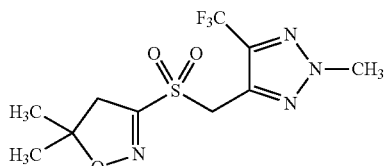

II.5

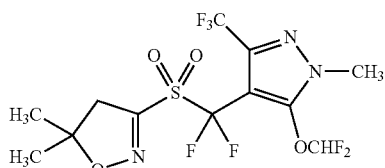

II.6

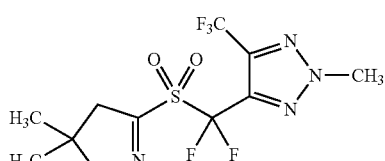

II.7

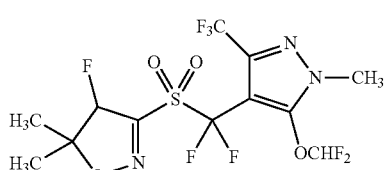

II.8

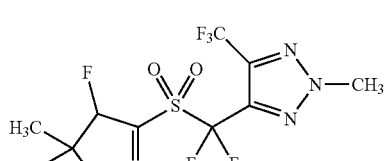

II.9

II.1

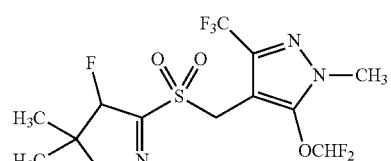

II.2

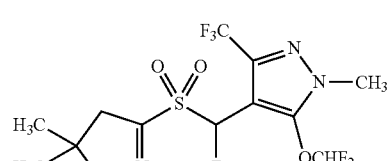

the isoxazoline compounds of the formula (I)I are known in the art, e.g. from WO 2006/024820, WO 2006/037945, WO 2007/071900 and WO 2007/096576;

among the VLCFA inhibitors, preference is given to chloroacetamides and oxyacetamides;

b11) from the group of the cellulose biosynthesis inhibitors:
chlorthiamid, dichlobenil, flupoxam, indaziflam, isoxaben, triaziflam and 1-cyclohexyl-5-pentafluorphenyloxy-1$^4$-[1,2,4,6]thiatriazin-3-ylamine (CAS 175899-01-1);

b12) from the group of the decoupler herbicides:
dinoseb, dinoterb and DNOC and its salts;

b13) from the group of the auxinic herbicides:
2,4-D and its salts and esters such as clacyfos, 2,4-DB and its salts and esters, aminocyclopyrachlor and its salts and esters, aminopyralid and its salts such as aminopyralid-dimethylammonium, aminopyralid-tris(2-hydroxypropyl) ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluroxypyr, fluroxypyr-butometyl, fluroxypyr-meptyl, halauxifen and its salts and esters (CAS 943832-60-8), e.g. halauxifen-methyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters and triclopyr and its salts and esters, 4-amino-3-chloro-6-(4-chloro-2-fluoro-3-methoxyphenyl)-5-fluoropyridine-2-carboxylic acid and its salts and esters, e.g. benzyl 4-amino-3-chloro-6-(4-chloro-2-fluoro-3-methoxyphenyl)-5-fluoropyridine-2-carboxylate (CAS 1390661-72-9);

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, (1RS,2SR,4SR)-1,4-epoxy-p-menth-2-yl 2-methylbenzyl ether, cumyluron, cyclopyrimorate (CAS 499223-49-3) and its salts and esters, dalapon, dazomet, difenzoquat, difenzoquat-metilsulfate, dimethipin, DSMA, dymron, endothal and its salts, etobenzanid, flurenol, flurenol-butyl, flurprimidol, fosamine, fosamine-ammonium, indanofan, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine and tridiphane.

Preference is given to those compositions according to the present invention comprising as the at least one further pesticide C a herbicide selected from glyphosate, glufosinate, clethodim, sethoxydim, quizalofop, fluazifop, imazamox, imazaquin, imazethapyr, cloransulam, diclosulam, flumetsulam, chlorimuron, thifensulfuron, metolachlor, acetochlor, dimethenamid, pyroxasulfone, fomesafen, lactofen, acifluorfen, bentazon, cinmethylin, naptalam, flumiclorac, pendimethalin, trifluralin, ethalfluralin, tribenuron, metribuzin, clomazone, flufenacet, saflufenacil, trifludimoxazin, linuron, diuron, paraquat, 2,4-D, diflufenzopyr, carfentrazone, flumioxazin, sulfentrazone, halosulfuron, iodosulfuorn, mesotrione, isoxaflutole, topramezone, tembotrione and bicyclopyrone.

Preference is also given to those compositions according to the present invention which comprise as the at least one further pesticide C a herbicide selected from glyphosate, glufosinate, clethodim, sethoxydim, quizalofop, fluazifop, imazamox, imazaquin, imazethapyr, cloransulam, diclosulam, flumetsulam, chlorimuron, thifensulfuron, metolachlor, acetochlor, dimethenamid, pyroxasulfone, fomesafen, lactofen, acifluorfen, bentazon, cinmethylin, naptalam and flumiclorac, particularly naptalam.

Preference is also given to those compositions according to the present invention which comprise as the at least one further pesticide C a herbicide selected from naptalam and dimethenamid.

Preference is also given to compositions according to the present invention which comprise as the at least one further pesticide C, wherein the pesticide C is a safener. Safeners are chemical compounds which prevent or reduce damage on useful plants without having a major impact on the herbicidal action of the herbicidal active components of the present compositions towards unwanted plants. They can be applied either before sowings (e.g. on seed treatments, shoots or seedlings) or in the pre-emergence application or post-emergence application of the useful plant. The safeners and the composition according to the invention can be applied simultaneously or in succession.

Examples of preferred safeners are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4), N-(2-Methoxybenzoyl)-4-[(methylaminocarbonyl)amino]benzenesulfonamide (CAS 129531-12-0), MG191 (2-dichloromethyl-2-methyl-1,3-dioxolane) or their salts and esters.

Especially preferred safeners are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4) and N-(2-Methoxybenzoyl)-4-[(methylaminocarbonyl)amino]benzene sulfonamide (CAS 129531-12-0) or their salts and esters.

Particularly preferred safeners are benoxacor, cloquintocet, cyprosulfamide, dichlormid, fenchlorazole, fenclorim, furilazole, isoxadifen, mefenpyr, naphtalic anhydride, 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4) and N-(2-methoxybenzoyl)-4-[(methylaminocarbonyl)amino]benzenesulfonamide (CAS 129531-12-0) or their salts and esters.

The pesticides C of groups b1) to b15) and the safeners are known herbicides and safeners, see, for example, The Compendium of Pesticide Common Names (http://www.alanwood.net/pesticides/); Farm Chemicals Handbook 2000 volume 86, Meister Publishing Company, 2000; B. Hock, C. Fedtke, R. R. Schmidt, Herbizide [Herbicides], Georg Thieme Verlag, Stuttgart 1995; W. H. Ahrens, Herbicide Handbook, 7th edition, Weed Science Society of America, 1994; and K. K. Hatzios, Herbicide Handbook, Supplement for the 7th edition, Weed Science Society of America, 1998. 2,2,5-Trimethyl-3-(dichloroacetyl)-1,3-oxazolidine [CAS No. 52836-31-4] is also referred to as R-29148. 4-(Dichloroacetyl)-1-oxa-4-azaspiro[4.5]decane [CAS No. 71526-07-3] is also referred to as AD-67 and MON 4660. As to the given mechanisms of action and classification of the active substances, see e.g. "HRAC, Classification of Herbicides According to Mode of Action", http://www.plantprotection.org/hrac/MOA.html). The assignment of the active compounds to the respective mechanisms of action is based on current knowledge. If several mechanisms of action apply to one active compound, this substance was only assigned to one mechanism of action.

Pesticides C and safeners having a carboxyl group can be employed in the form of the acid, in the form of a salt as mentioned above or else in the form of an agriculturally acceptable derivative in the compositions according to the invention.

Suitable salts of 2,4-D are 2,4-D-ammonium, 2,4-D-dimethylammonium, 2,4-D-diethylammonium, 2,4-D-diethanolammonium (2,4-D-diolamine), 2,4-D-triethanolammonium, 2,4-D-isopropylammonium, 2,4-D-triisopropanolammonium, 2,4-D-heptylammonium, 2,4-D-dodecylammonium, 2,4-D-tetradecylammonium, 2,4-D- triethylammonium, 2,4-D-tris(2-hydroxypropyl) ammonium, 2,4-D-tris(isopropyl)ammonium, 2,4-D-trolamine, 2,4-D-lithium, 2,4-D-sodium. Examples of suitable esters of 2,4-D are 2,4-D-butotyl, 2,4-D-2-butoxypropyl, 2,4-D-3-butoxypropyl, 2,4-D-butyl, 2,4-D-ethyl, 2,4-D-ethylhexyl, 2,4-D-isobutyl, 2,4-D-isooctyl, 2,4-D-isopropyl, 2,4-D-meptyl, 2,4-D-methyl, 2,4-D-octyl, 2,4-D-pentyl, 2,4-D-propyl, 2,4-D-tefuryl and clacyfos.

Suitable salts of dichlorprop are for example dichlorprop-sodium, dichlorprop-potassium and dichlorprop-dimethylammonium. Examples of suitable esters of dichlorprop are dichlorprop-butotyl and dichlorprop-isoctyl.

Suitable salts and esters of MCPA include MCPA-butotyl, MCPA-butyl, MCPA-dimethyl-ammonium, MCPA-diolamine, MCPA-ethyl, MCPA-thioethyl, MCPA-2-ethylhexyl, MCPA-isobutyl, MCPA-isoctyl, MCPA-isopropyl, MCPA-isopropylammonium, MCPA-methyl, MCPA-olamine, MCPA-potassium, MCPA-sodium and MCPA-trolamine.

A suitable salt of MCPB is MCPB sodium. A suitable ester of MCPB is MCPB-ethyl.

Suitable salts of clopyralid are clopyralid-potassium, clopyralid-olamine and clopyralid-tris-(2-hydroxypropyl) ammonium. Example of suitable esters of clopyralid is clopyralid-methyl. Examples of a suitable ester of fluroxypyr are fluroxypyr-meptyl and fluroxypyr-2-butoxy-1-methylethyl, wherein fluroxypyr-meptyl is preferred.

Suitable salts of picloram are picloram-dimethylammonium, picloram-potassium, picloram-triisopropanolammonium, picloram-triisopropylammonium and picloram-trolamine. A suitable ester of picloram is picloram-isoctyl.

A suitable salt of triclopyr is triclopyr-triethylammonium. Suitable esters of triclopyr are for example triclopyr-ethyl and triclopyr-butotyl.

Suitable salts and esters of chloramben include chloramben-ammonium, chloramben-diolamine, chloramben-methyl, chloramben-methylammonium and chloramben-sodium. Suitable salts and esters of 2,3,6-TBA include 2,3,6-TBA-dimethylammonium, 2,3,6-TBA-lithium, 2,3,6-TBA-potassium and 2,3,6-TBA-sodium.

Suitable salts and esters of aminopyralid include aminopyralid-potassium, aminopyralid-dimethylammonium, and aminopyralid-tris(2-hydroxypropyl)ammonium.

Suitable salts of glyphosate are for example glyphosate-ammonium, glyphosate-diammonium, glyphoste-dimethylammonium, glyphosate-isopropylammonium, glyphosate-potassium, glyphosate-sodium, glyphosate-trimesium as well as the ethanolamine and diethanolamine salts, preferably glyphosate-diammonium, glyphosate-isopropylammonium and glyphosate-trimesium (sulfosate).

A suitable salt of glufosinate is for example glufosinate-ammonium.

A suitable salt of glufosinate-P is for example glufosinate-P-ammonium.

Suitable salts and esters of bromoxynil are for example bromoxynil-butyrate, bromoxynil-heptanoate, bromoxynil-octanoate, bromoxynil-potassium and bromoxynil-sodium.

Suitable salts and esters of ioxonil are for example ioxonil-octanoate, ioxonil-potassium and ioxonil-sodium.

Suitable salts and esters of mecoprop include mecoprop-butotyl, mecoprop-dimethylammonium, mecoprop-diolamine, mecoprop-ethadyl, mecoprop-2-ethylhexyl, mecoprop-isoctyl, mecoprop-methyl, mecoprop-potassium, mecoprop-sodium and mecoprop-trolamine.

Suitable salts of mecoprop-P are for example mecoprop-P-butotyl, mecoprop-P-dimethylammonium, mecoprop-P-2-ethylhexyl, mecoprop-P-isobutyl, mecoprop-P-potassium and mecoprop-P-sodium.

A suitable salt of diflufenzopyr is for example diflufenzopyr-sodium.

A suitable salt of naptalam is for example naptalam-sodium or naptalam-N,N-bis-(3-aminopropyl)methylamine.

Suitable salts and esters of aminocyclopyrachlor are for example aminocyclopyrachlor-dimethylammonium, aminocyclopyrachlor-methyl, aminocyclopyrachlor-triisopropanolammonium, aminocyclopyrachlor-sodium and aminocyclopyrachlor-potassium.

A suitable salt of quinclorac is for example quinclorac-dimethylammonium.

A suitable salt of quinmerac is for example quinmerac-dimethylammonium.

A suitable salt of imazamox is for example imazamox-ammonium.

Suitable salts of imazapic are for example imazapic-ammonium and imazapic-isopropylammonium.

Suitable salts of imazapyr are for example imazapyr-ammonium and imazapyr-isopropylammonium.

A suitable salt of imazaquin is for example imazaquin-ammonium.

Suitable salts of imazethapyr are for example imazethapyr-ammonium and imazethapyr-isopropylammonium.

A suitable salt of topramezone is for example topramezone-sodium.

Here and below, the term "binary compositions" refers to compositions comprising components A) and B) according to the invention.

Correspondingly, the term "ternary compositions" refers to compositions comprising components A) and B) according to the invention and at least one further pesticide C. The term "acid equivalent" as used herein is defined as that portion of a formulation (as in the case of a 2,4-DB salt) that theoretically could be converted back to the corresponding or parent acid.

In binary compositions, the weight ratio of the active components A) to B) based on acid equivalents for controlling unwanted vegetation and to achieve over additive effects is in the range of from 1:2 to 1:50, or in the range of from 1:6 to 1:50, or in the range of from 1:8 to 1:50, or in the range of from 1:6 to 1:24, or in the range of from 1:8 to 1:24, or in the range of from 1:12 to 1:100, or in the range of from 1:12 to 1:50, or in the range of from 1:12 to 1:24.

In ternary compositions the relative proportions by weight of the active components A) to B) based on acid equivalents for controlling unwanted vegetation and to achieve over additive effects is as described above for binary compositions; the weight ratio of the components A) to the at least one further pesticide C based on acid equivalents is generally in the range of from 1:1000 to 1000:1, preferably in the range of from 1:500 to 500:1, in particular in the range of from 1:250 to 250:1 and also preferably in the range of from 1:20 to 20:1 or in the range from 1:5 to 5:1, or in the range from 1:2 to 2:1, and the weight ratio of the components B:C is generally in the range of from 1:1000 to 1000:1, preferably in the range of from 1:500 to 500:1, in particular in the range of from 1:250 to 250:1 and also preferably in the range of from 1:20 to 20:1 or in the range from 1:5 to 5:1, or in the range from 1:2 to 2:1. The weight ratio of components A+B to component C based on acid equivalents is preferably in the range of from 1:500 to 500:1, in particular in the range of from 1:250 to 250:1 and also preferably in the range of from 1:20 to 20:1 or in the range from 1:5 to 5:1, or in the range from 1:2 to 2:1.

When employed for controlling unwanted vegetation and to achieve over additive effects, the total amounts of components A) and B) applied, without formulation auxiliaries, are typically from 0.1 to 5 kg a.i./hectare (ha), or from 0.1 to 2 kg a.i./ha, or from 0.3 to 1.3 kg a.i./ha, or from 0.3 to 0.8 kg a.i./ha, or from 0.3 to 0.7 kg a.i./ha, or from 0.4 to 0.6 kg a.i./ha based on acid equivalents.

In one aspect of the invention, when employed for controlling unwanted vegetation and to achieve over additive effects, the total amounts of components A) and B) applied, without formulation auxiliaries, is from 0.3 to 1.3 kg a.i./ha and the weight ratio of the active components A) to B) for controlling unwanted vegetation and to achieve over additive effects is in the range of from 1:2 to 1:50, or in the range of from 1:6 to 1:50, or in the range of from 1:8 to 1:50, or in the range of from 1:6 to 1:24, or in the range of from 1:8 to 1:24, or in the range of from 1:12 to 1:100, or in the range of from 1:12 to 1:50, or in the range of from 1:12 to 1:24, based on acid equivalents.

In another aspect of the invention, when employed for controlling unwanted vegetation and to achieve over additive effects, the total amounts of components A) and B) applied, without formulation auxiliaries, is from 0.3 to 0.7 kg a.i./ha, and the weight ratio of the active components A) to B) for controlling unwanted vegetation and to achieve over additive effects is in the range of from 1:2 to 1:50, or in the range of from 1:6 to 1:50, or in the range of from 1:8 to 1:50, or in the range of from 1:6 to 1:24, or in the range of from 1:8 to 1:24, or in the range of from 1:12 to 1:100, or in the range of from 1:12 to 1:50, or in the range of from 1:12 to 1:24, based on acid equivalents.

The rates of application of the component A) according to the present invention (total amount of 2,4-DB) based on acid equivalents are in the range from 10 g a.i./ha to 250 g a.i./ha, or from 15 g a.i./ha to 75 g a.i./ha, or from 30 g a.i./ha to 60 g a.i./ha.

The typical rates of application of the component B) according to the present invention (total amount of dicamba) based on acid equivalents are in the range from 100 g a.i./ha to 2000 g a.i./ha, or from 250 kg a.i./ha to 1200 g a.i./ha, or from 400 g a.i./ha to 600 g a.i./ha.

The compositions according to the invention are suitable for herbicidal use as such or as an appropriately formulated composition (agrochemical composition).

The compositions used according to the invention can be converted into customary types of agrochemical compositions, e. g. solutions, emulsions, suspensions, dusts, powders, pastes, granules, pressings, capsules, and mixtures thereof. An agrochemical composition comprises a pesticidally effective amount of a composition according to the invention. The term "effective amount" denotes an amount of the active ingredients, which is sufficient for controlling unwanted vegetation, especially for controlling unwanted plants in cultivated plants, and which does not result in a substantial damage to the treated plants. Such an amount can vary in a broad range and is dependent on various factors, such as the plants to be controlled, the treated cultivated plant or material, the climatic conditions and the specific composition according to the invention used.

Examples for agrochemical composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further agrochemical compositions types are defined in the "Catalogue of pesticide formulation types and international coding system", Technical Monograph No. 2, $6^{th}$ Ed. May 2008, CropLife International.

The agrochemical compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers, drift control agents and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharides, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emulsifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylarylsulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinylalcohols, or vinylacetate.

In one aspect of the invention, when employed for controlling unwanted vegetation and to achieve over additive effects, the aqueous herbicidal compositions are used in the presence of a non-ionic surfactant.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compound I on the target. Examples are surfactants, mineral or vegetable oils, and other auxiliaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), inorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Suitable Drift control agents may be understood as chemical agents, which reduce the wind drift when spraying an aqueous tank mix composition. Water soluble polymers, particularly polysaccharide polymers, such as, for example, guar, guar derivatives, and poly(acrylamide) polymers are known to be effective as drift control agents. Other examples of drift control agents are lecithin derivatives, linear non-ionic polymers with a molecular weight of at least 20 kDa or fatty alcohol alkoxylates; preferred fatty alcohol alkoxylates are fatty alcohol ethoxylates. The fatty alcohol may comprise a $C_{12-22}$, preferably a $C_{14-20}$, and in particular a $C_{16-18}$ fatty alcohol. The fatty alcohol ethoxylate may comprise from 1 to 15, preferably from 1 to 8, and in particular from 2 to 6 equivalents of ethylene oxide. Especially suitable fatty alcohol ethoxylate is a $C_{14-20}$ fatty alcohol, which comprises from 2 to 6 equivalents of ethylene oxide. Drift control agents are commercially available from various companies (tradenames of the products given in brackets): Ag Spray, Inc. (Halt), Ashland Specialty Ingredients (Soilcare), Brewer International Inc. (Poly Control 2), Conklin Co. Inc. (Complete), Helena Chemical Co. (AccuQuest WM, AccuZone DC, Grounded, On-Line, Sta Put, Strike Zone, LineMan), Intracrop (Driftless), Kalo, Inc. (One AP XL, Spectra Tank Mix, Spectra Max), Loveland Products, Inc. (LI 700), Nalco Co. (Staput Plus), Precision Laboratories, Inc. (Border, Border Xtra, Direct, Transport Plus), Rhodia Inc. (AgRHO DEP, AgRHO DR), Sanitek Products, Inc. (SANAG Div.) (41-A, 38-F), Willowood USA (Willowood Driftguard), FORMULA-40 TORS' TRADE NAMES: Brandt Consolidated, Inc. (Drift Free), Custom Agricultural Formulators (Driftstop), Loveland Products, Inc. (Compadre, Liberate, Reign, Reign LC, Weather Gard Complete), Wilbur-Ellis Co. (Bronc Max EDT, EDT Concentrate, In-Place), Winfield Solutions, LLC (Arrow four, Corral AMS, Interlock, Placement Propak, Powerlock), and various other discontinued commercial products, such as Apasil, Bivert, Chem-Trol, Confine, Corral Poly, Drifgon, Driftgard, Drop Zone, Intac Plus, Nalcotrol, Nalcotrol 11, Nalquatic, Progacyl, Target, TMP, Wind-Fall.

Other agents for reducing wind drift may be applied comprising a salt selected from the group consisting of:

(a) an ammonium salt of Formula (III)

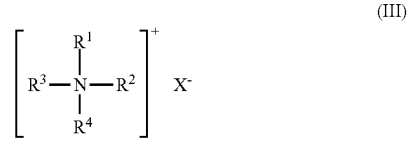

(III)

wherein $R^1$, $R^2$, $R^3$ and $R^4$ are independently a saturated or partially unsaturated $C_1$-$C_{12}$ hydrocarbyl and X is an agronomically acceptable anion; for example, the salt of Formula (III) is selected from the group consisting of tetraethylammonium chloride, tributylmethylammonium chloride, tetrabutylammonium chloride, tetrabutylammonium bromide, benzalconium chloride and dodecyltrimethylammonium chloride;

(b) a salt containing a nitrogen heterocycle of Formula (IV)

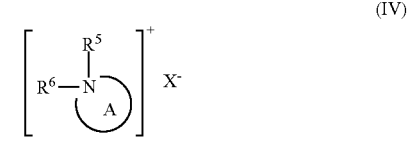

(IV)

wherein A is a 5 or 6-membered saturated or partially unsaturated heterocyclic ring comprising, as ring member atom, at least one quarternary nitrogen atom; and wherein the quarternary nitrogen atom carries two substituents $R^5$ and $R^6$, wherein $R^5$ is a $C_1$-$C_{20}$ alkyl radical; $R^6$ is hydrogen or a $C_1$-$C_6$ alkyl radical; and wherein X is an agronomically acceptable anion; for example, the salt of Formula (IV) is selected from the group consisting of methylimidazolium chloride, octylimmidazolium chloride, 1-butyl-1-methyl-pyrrolidinium chloride, 1-ethyl-3-methylimidazolium chloride, 1-butyl-3-methylimidazolium chloride, 1-methyl-3-octylimidazolium chloride, cetylpyridinium chloride and cetylpyridinium bromide.

(c) a phosphonium salt of Formula (V)

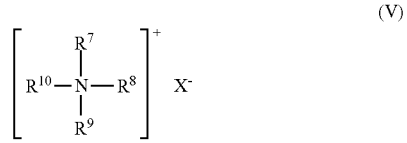

(V)

wherein $R^7$, $R^8$, $R^9$ and $R^{10}$ are independently a $C_1$-$C_{12}$ hydrocarbyl and X is an agronomically acceptable anion; and mixtures thereof; for example, the salt of Formula (V) is tetrabutylphosphonium chloride.

Examples for agrochemical composition types and their preparation are:

i) Water-Soluble Concentrates (SL, LS)

10-60 wt % of a composition according to the invention and 5-15 wt % wetting agent (e.g. alcohol alkoxylates) are dissolved in water and/or in a water-soluble solvent (e.g. alcohols) ad 100 wt %. The active substance dissolves upon dilution with water.

ii) Dispersible Concentrates (DC)

5-25 wt % of a composition according to the invention and 1-10 wt % dispersant (e. g. polyvinylpyrrolidone) are dissolved in organic solvent (e.g. cyclohexanone) ad 100 wt %. Dilution with water gives a dispersion.

iii) Emulsifiable Concentrates (EC)

15-70 wt % of a composition according to the invention and 5-10 wt % emulsifiers (e.g. calcium dodecylbenzenesulfonate and castor oil ethoxylate) are dissolved in water-insoluble organic solvent (e.g. aromatic hydrocarbon) ad 100 wt %. Dilution with water gives an emulsion.

iv) Emulsions (EW, EO, ES)

5-40 wt % of a composition according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into water ad 100 wt % by means of an emulsifying machine and made into a homogeneous emulsion. Dilution with water gives an emulsion.

v) Suspensions (SC, OD, FS)

In an agitated ball mill, 20-60 wt % of a composition according to the invention are comminuted with addition of 2-10 wt % dispersants and wetting agents (e.g. sodium lignosulfonate and alcohol ethoxylate), 0.1-2 wt % thickener (e.g. xanthan gum) and water ad 100 wt % to give a fine active substance suspension. Dilution with water gives a stable suspension of the active substance. For FS type composition up to 40 wt % binder (e.g. polyvinylalcohol) is added.

vi) Water-Dispersible Granules and Water-Soluble Granules (WG, SG)

50-80 wt % of a composition according to the invention are ground finely with addition of dispersants and wetting agents (e.g. sodium lignosulfonate and alcohol ethoxylate) ad 100 wt % and prepared as water-dispersible or water-soluble granules by means of technical appliances (e. g. extrusion, spray tower, fluidized bed). Dilution with water gives a stable dispersion or solution of the active substance.

vii) Water-Dispersible Powders and Water-Soluble Powders (WP, SP, WS)

50-80 wt % of a composition according to the invention are ground in a rotor-stator mill with addition of 1-5 wt % dispersants (e.g. sodium lignosulfonate), 1-3 wt % wetting agents (e.g. alcohol ethoxylate) and solid carrier (e.g. silica gel) ad 100 wt %. Dilution with water gives a stable dispersion or solution of the active substance.

viii) Gel (GW, GF)

In an agitated ball mill, 5-25 wt % of a composition according to the invention are comminuted with addition of 3-10 wt % dispersants (e.g. sodium lignosulfonate), 1-5 wt % thickener (e.g. carboxymethylcellulose) and water ad 100 wt % to give a fine suspension of the active substance. Dilution with water gives a stable suspension of the active substance.

ix) Microemulsion (ME)

5-20 wt % of a composition according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water ad 100%. This mixture is stirred for 1 h to produce spontaneously a thermodynamically stable microemulsion.

x) Microcapsules (CS)

An oil phase comprising 5-50 wt % of a composition according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radical initiator results in the formation of poly(meth)acrylate microcapsules. Alternatively, an oil phase comprising 5-50 wt % of a compound I according to the invention, 0-40 wt % water insoluble organic solvent (e.g. aromatic hydrocarbon), and an isocyanate monomer (e.g. diphenylmethene-4,4'-diisocyanate) are dispersed into an aqueous solution of a protective colloid (e.g. polyvinyl alcohol). The addition of a polyamine (e.g. hexamethylenediamine) results in the formation of polyurea microcapsules. The monomers amount to 1-10 wt %. The wt % relate to the total CS composition.

xi) Dustable Powders (DP, DS)

1-10 wt % of a composition according to the invention are ground finely and mixed intimately with solid carrier (e.g. finely divided kaolin) ad 100 wt %.

xii) Granules (GR, FG)

0.5-30 wt % of a composition according to the invention is ground finely and associated with solid carrier (e.g. silicate) ad 100 wt %. Granulation is achieved by extrusion, spray-drying or the fluidized bed.

xiii) Ultra-Low Volume Liquids (UL)

1-50 wt % of a composition according to the invention are dissolved in organic solvent (e.g. aromatic hydrocarbon) ad 100 wt %.

The agrochemical composition types i) to xiii) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and in particular between 0.5 and 75%, by weight of active substance. The active substances are employed in a purity of from 90% to 100%, preferably from 95% to 100% (according to NMR spectrum).

Solutions for seed treatment (LS), suspoemulsions (SE), flowable concentrates (FS), powders for dry treatment (DS), water-dispersible powders for slurry treatment (WS), water-soluble powders (SS), emulsions (ES), emulsifiable concentrates (EC) and gels (GF) are usually employed for the purposes of treatment of plant propagation materials, particularly seeds. The compositions in question give, after two-to-tenfold dilution, active substance concentrations of from 0.01 to 60% by weight, preferably from 0.1 to 40% by weight, in the ready-to-use preparations. Application can be carried out before, after or during sowing.

Various types of oils, wetters, adjuvants, fertilizer, or micronutrients, and further pesticides (e.g. herbicides, insecticides, fungicides, growth regulators, safeners) may be added to the composition comprising components A) and B) or comprising them as premix or, if appropriate not until immediately prior to use (tank mix). These agents can be admixed with the compositions according to the invention in a weight ratio of 1:100 to 100:1, preferably 1:10 to 10:1.

The user applies the agrochemical composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area. According to one embodiment, either individual components of the agrochemical composition according to the invention or partially premixed components, e. g. components A) and B) and, optionally a pesticide C, may be mixed by the user in a spray tank and further auxiliaries and additives may be added, if appropriate.

In a further embodiment, individual components of the agrochemical composition according to the invention such as parts of a kit or parts of a binary or ternary mixture may be mixed by the user himself in a spray tank and further auxiliaries may be added, if appropriate.

In a further embodiment, either individual components of the agrochemical composition according to the invention or partially premixed components, e. g. components A) and B) and, optionally a pesticide C, can be applied jointly (e.g. after tank mix) or consecutively.

The use of herbicidal compositions according to the invention controls unwanted vegetation on non-crop areas very efficiently, especially at high rates of application. They act against broad-leafed weeds and grass weeds in crops such as wheat, rice, corn, soybeans and cotton without causing any significant damage to the crop plants. This effect is mainly observed at low rates of application.

The method of using herbicidal compositions according to the invention is effected through the step of applying the composition to the plants mainly by spraying the leaves. Here, the application can be carried out using, for example, water as carrier by customary spraying techniques using spray liquor amounts of from about 100 to 1000 liter/ha (for example from 100 to 400 liter/ha). The herbicidal compositions may also be applied by the low-volume or the ultra-low-volume method, or in the form of microgranules. Application of the herbicidal compositions according to the present invention can be done before, during and/or after, preferably during and/or after, the emergence of the undesirable plants.

The herbicidal compositions according to the present invention can be applied pre- or post-emergence or together with the seed of a crop plant. In one aspect of the invention the herbicidal compositions according to the present invention is applied post-emergence. It is also possible to apply the compositions by applying seed, pretreated with a composition of the invention, of a crop plant. If the active components A) and B), and, optionally, at least one further pesticides C, are less well tolerated by certain crop plants, application techniques may be used in which the herbicidal compositions are sprayed, with the aid of the spraying equipment, in such a way that as far as possible they do not come into contact with the leaves of the sensitive crop plants, while the active compounds reach the leaves of undesirable plants growing underneath, or the bare soil surface (post-directed, lay-by).

Moreover, it may be advantageous to apply the composition according to the invention comprising component A) and B) and, optionally a further pesticide C, on their own or jointly in combination with other crop protection agents, for example with agents for controlling pests or phytopathogenic fungi or bacteria or with groups of active compounds which regulate growth. Also of interest is the miscibility with mineral salt solutions which are employed for treating nutritional and trace element deficiencies. Non-phytotoxic oils and oil concentrates can also be added.

In the use and methods of the present invention it is immaterial whether the component A), and the component B) and, optionally, the further pesticide C or safener are formulated and applied jointly or separately. In the case of separate application it is of minor importance, in which order the application takes place. It is only necessary, that the components of the composition are applied in a time frame that allows simultaneous action of the active ingredients on the plants, preferably within a time-frame of at most 14 days, in particular at most 7 days.

The compositions according to the invention are suitable as herbicides. They are distinguished by an outstanding effectiveness against a broad spectrum of weed species, including Velvetleaf (*Abutilon theophrasti*), morningglory (*Ipomoea* spp.), Giant ragweed (*Ambrosia trifida*), Common ragweed (*Ambrosia artemisiifolia*), Common Sunflower (*Helianthus annuus*), Marestail/horseweed/fleabane (*Conyza* spp.), Burcucumber (*Sicyos angulatus*), hemp dogbane (*Apocynum cannabinum*), Canada thistle (*Cirsium arvense*), Eastern black nightshade (*Solanum ptycanthum*), Black nightshade (*Solanum nigrum*), Cocklebur (*Xanthium* spp.), Beggarticks (*Bidens pilosa*), Dayflower (*Commelina* spp.), Pellitory (*Parietaria debilis*), Globe mallow (*Sphaeralcea bonariensis*), Sowthistle (*Sonchus* spp.), Field bindweed (*Convolvulus arvensis*), copperleaf (*Acalypha* spp.), Eveningprimrose (*Oenothera* spp.), Dandelion (*Taraxacum officinale*), Field Violet (*Viola* spp.), Juba's bush (*Iresine diffusa*), bugloss (*Anchusa arvensis*), Vervain (*Verbena* spp.), *Sida* (*Sida* spp.), Spurge (*Euphorbia* spp.), Button weed/broom (*Spermacoce* spp.).

In one aspect the compositions according to the invention are suitable as herbicides especially in soybean as the crop plant, which derive from the family of Amaranthaceae, for example the classes of Amaranthus (for example Amaranthus palmeri, Amaranthus tuberculatus, Amaranthus rudis, Amaranthus retroflexus, Amaranthus hybridus, Amaranthus powellii, Amaranthus spinosus and Amaranthus blitoides), and the subfamily Chenopodiaceae (for example Chenopodium album or Kochia (for example Kochia scoparia)).

In one aspect the herbicidal use of compositions according to the invention relates to the control of Amaranthus palmeri, Amaranthus tuberculatus and Amaranthus rudis.

Depending on the application method in question, the compositions according to the invention can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Bras-* sica napus var. napobrassica, Brassica rapa var. silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus spec., Manihot esculenta, Medicago sativa, Musa spec., Nicotiana tabacum (N.rustica), Olea europaea, Oryza sativa, Phaseolus lunatus, Phaseolus vulgaris, Picea abies, Pinus spec., Pistacia vera, Pisum sativum, Prunus avium, Prunus persica, Pyrus communis, Prunus armeniaca, Prunus cerasus, Prunus dulcis and Prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera, Zea mays.

Especially preferred crop plants are crops of cereals, corn, soybeans, rice, millets, oilseed rape, cotton, sugarcane, potatoes, legumes, turf or permanent crops, particularly of soybeans.

The compositions according to the invention can also be used in genetically modified plants. The term "genetically modified plants" is to be understood as plants whose genetic material has been modified by the use of recombinant DNA techniques to include an inserted sequence of DNA that is not native to that plant species' genome or to exhibit a deletion of DNA that was native to that species' genome, wherein the modification(s) cannot readily be obtained by cross breeding, mutagenesis or natural recombination alone. Often, a particular genetically modified plant will be one that has obtained its genetic modification(s) by inheritance through a natural breeding or propagation process from an ancestral plant whose genome was the one directly treated by use of a recombinant DNA technique. Typically, one or more genes have been integrated into the genetic material of a genetically modified plant in order to improve certain properties of the plant. Such genetic modifications also include but are not limited to targeted post-translational modification of protein(s), oligo- or polypeptides, e. g., by inclusion therein of amino acid mutation(s) that permit, decrease, or promote glycosylation or polymer additions such as prenylation, acetylation farnesylation, or PEG moiety attachment.

Plants that have been modified by breeding, mutagenesis or genetic engineering, e.g. have been rendered tolerant to applications of specific classes of herbicides, such as auxinic herbicides such as dicamba or 2,4-D; bleacher herbicides such as 4-hydroxyphenylpyruvate dioxygenase (HPPD) inhibitors or phytoene desaturase (PDS) inhibitors; acetolactate synthase (ALS) inhibitors such as sulfonylureas or imidazolinones; enolpyruvyl shikimate 3-phosphate synthase (EPSP) inhibitors such as glyphosate; glutamine synthetase (GS) inhibitors such as glufosinate; protoporphyrinogen-IX oxidase inhibitors (PPO); lipid biosynthesis inhibitors such as acetylCoA carboxylase (ACCase) inhibitors; or oxynil (i. e. bromoxynil or ioxynil) herbicides as a result of conventional methods of breeding or genetic engineering; furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, ACCase inhibitors or auxinic herbicides, in particular dicamba, 2,4-D or 2,4-DB; most particularly dicamba.

Accordingly one embodiment of the invention relates to the use of compositions according to the invention, wherein the crop plants are tolerant or resistant to dicamba (component B) and/or 2,4-DB (component A).

These herbicide resistance technologies are, for example, described in Pest Management Science 61, 2005, 246; 61, 2005, 258; 61, 2005, 277; 61, 2005, 269; 61, 2005, 286; 64, 2008, 326; 64, 2008, 332; Weed Science 57, 2009, 108; Australian Journal of Agricultural Research 58, 2007, 708; Science 316, 2007, 1185; and references quoted therein. Several cultivated plants have been rendered tolerant to herbicides by mutagenesis and conventional methods of breeding, e. g., Clearfield® summer rape (Canola, BASF SE, Germany) being tolerant to imidazolinones, e. g., imazamox, or ExpressSun® sunflowers (DuPont, USA) being tolerant to sulfonyl ureas, e. g., tribenuron. Genetic engineering methods have been used to render cultivated plants such as soybean, cotton, corn, beets and rape, tolerant to herbicides such as glyphosate, imidazolinones and glufosinate, some of which are under development or commercially available under the brands or trade names RoundupReady® (glyphosate tolerant, Monsanto, USA), Cultivance® (imidazolinone tolerant, BASF SE, Germany) and LibertyLink® (glufosinate tolerant, Bayer CropScience, Germany).

Furthermore, plants are also covered that are by the use of recombinant DNA techniques capable to synthesize one or more insecticidal proteins, especially those known from the bacterial genus Bacillus, particularly from Bacillus thuringiensis, such as delta-endotoxins, e. g., CryIA(b), CryIA(c), CryIF, CryIF(a2), CryIIA(b), CryIIIA, CryIIIB(b1) or Cry9c; vegetative insecticidal proteins (VIP), e. g., VIP1, VIP2, VIP3 or VIP3A; insecticidal proteins of bacteria colonizing nematodes, e. g., Photorhabdus spp. or Xenorhabdus spp.; toxins produced by animals, such as scorpion toxins, arachnid toxins, wasp toxins, or other insect-specific neurotoxins; toxins produced by fungi, such as Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxy-steroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be understood expressly also as including pre-toxins, hybrid proteins, truncated or otherwise modified proteins. Hybrid proteins are characterized by a new combination of protein domains, (see, e. g., WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e. g., in the publications mentioned above. These insecticidal proteins contained in the genetically modified plants impart to the plants producing these proteins tolerance to harmful pests from all taxonomic groups of arthropods, especially to beetles (Coleoptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g., Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme). Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g., EP-A 392 225), plant disease resistance genes (e. g., potato culti-vars, which express resistance genes acting against *Phytophthora infestans* derived from the Mexican wild potato, *Solanum bulbocastanum*) or T4-lyso-zym (e.g., potato cultivars capable of synthesizing these proteins with increased resistance against bacteria such as *Erwinia amylovora*). The methods for producing such genetically modified plants are generally known to the person skilled in the art and are described, e.g., in the publications mentioned above.

Furthermore, plants are also covered that are by the use of recombinant DNA techniques capable to synthesize one or more proteins to increase the productivity (e.g., bio-mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of ingredients or new ingredients, specifically to improve human or animal nutrition, e. g., oil crops that produce health-promoting long-chain omega-3 fatty acids or unsaturated omega-9 fatty acids (e. g., Nexera® rape, Dow AgroSciences, Canada). Furthermore, plants are also covered that contain by the use of recombinant DNA techniques a modified amount of ingredients or new ingredients, specifically to improve raw material production, e.g., potatoes that produce increased amounts of amylopectin (e.g. Amflora® potato, BASF SE, Germany).

Furthermore, it has been found that the use of the herbicidal composition according to the invention is also suitable for the defoliation and/or desiccation of plant parts, for which crop plants such as cotton, potato, oilseed rape, sunflower, soybean or field beans, in particular cotton, are suitable. In this regard compositions have been found for the desiccation and/or defoliation of plants, processes for preparing these compositions, and methods for desiccating and/or defoliating plants using the compositions according to the invention.

As desiccants, the compositions according to the invention are suitable in particular for desiccating the above-ground parts of crop plants such as potato, oilseed rape, sunflower, cereals and soybean. This makes possible the fully mechanical harvesting of these important crop plants.

Also of economic interest is the facilitation of harvesting, which is made possible by concentrating within a certain period of time the dehiscence, or reduction of adhesion to the tree, in citrus fruit, olives and other species and varieties of pomaceous fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

USE EXAMPLES

The following examples summarized in table 1 serve to illustrate the invention:

Dicamba was applied as Engenia™ herbicide [BAPMA salt-(bis(3-aminopropyl)methylamine))], while 2,4-DB was applied as the commercially available Butyrac® 200 (dimethylamine salt). Herbicides were applied at an appropriate weight of each product dissolved in 1 liter of water. All herbicide treatments were applied with 0.25% by volume of a non-ionic surfactant (Induce®; an adjuvant composition consisting of alkyl aryl polyoxyalkane ethers, alkanolamides, dimethyl siloxane and free fatty acids). The spray solution was applied by a $CO_2$ powered backpack sprayer delivering the spray solution at a rate of 185 liter/ha. The spray solution was applied to a field naturally populated with Palmer amaranth (Amaranthus palmeri) with an average height of 4-6 inches in height, however, plants both larger and smaller plants were in the field at the time of application as well. Palmer amaranth was assessed for visual injury 3 days after treatment and injury was rated on a scale from 0 to 100, whereby 0 equals no herbicidal response and 100 equals complete control of the Palmer amaranth.

TABLE 1

| | | | herbicidal activity against Amaranthus palmeri (% control) | |
|---|---|---|---|---|
| Exp. | application rate a.i. in g/ha | | Calculated (additive | |
| No. | dicamba | 2,4-DB | effect) | found |
| 1 | 420 | — | — | 60 |
| 2 | — | 17.5 | — | 0 |
| 3 | — | 35 | — | 5 |
| 4 | — | 52.5 | — | 15 |
| 5 | 420 | 17.5 | 60 | 75 |
| 6 | 420 | 35 | 65 | 70 |
| 7 | 420 | 52.5 | 75 | 70 |

The invention claimed is:
1. A method for controlling unwanted vegetation in crop plants, which comprises treating plants, their seeds and/or their habitat with a herbicidal composition comprising as component

A) 4-(2,4-dichlorophenoxy)butanoic acid of formula (I) or salts or esters thereof

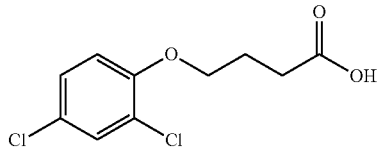
(I)

and as component
B) 3,6-dichloro-2-methoxybenzoic acid of formula (II) or salts or esters thereof,

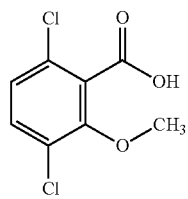
(II)

wherein the weight ratio of components A) to B) based on acid equivalents is from 1:12 to 1:50.

2. The method of claim 1, wherein the weight ratio of components A) to B) based on acid equivalents is from 1:12 to 1:24.

3. The method of claim 1, wherein the composition comprises components A) and B) in a total amount of from 300 to 1300 g of active ingredients per hectar based on acid equivalents.

4. The method of claim 1, wherein the component B) is dicamba-N,N-bis-(3-aminopropyl)methylamine salt or dicamba-diethylenetriamine salt.

5. The method of claim 1, wherein the component A) and the component B) are the respective N,N-bis-(3-aminopropyl)methylamine salt or diethylenetriamine salt.

6. The method of claim 1, wherein the crop plant is soybean.

7. The method of claim 1, wherein the unwanted vegetation to be controlled is selected from the family of Amaranthaceae.

8. The method of claim 1, wherein the unwanted vegetation to be controlled is selected from the class of Amaranthus.

9. The method of claim 1, wherein the crop plants are tolerant or resistant to component A) and/or component B).

10. A method for controlling unwanted vegetation in crop plants, which comprises applying simultaneously, separately, or in succession:

component
A) 4-(2,4-dichlorophenoxy)butanoic acid of formula (I) or salts or esters thereof

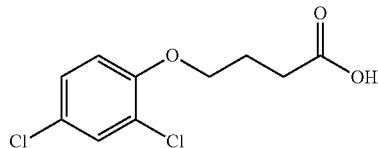 [SMILES: O=C(O)CCCOc1ccc(Cl)cc1Cl]
(I)

and component
B) 3,6-dichloro-2-methoxybenzoic acid formula (II) or salts or esters thereof,

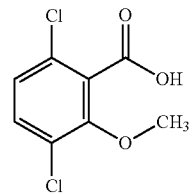
(II)

at a weight ratio of components A) to B) based on acid equivalents of from 1:12 to 1:50; on plants, their seeds, or their habitat.

11. A method as claimed in claim 10, wherein the compounds are applied after emergence of the crop plant.

12. The method of claim 10, wherein the weight ratio of components A) to B) based on acid equivalents is from 1:12 to 1:24.

13. The method of claim 10, a total amount of from 300 to 1300 g of active ingredients per hectar based on acid equivalents.

14. The method of claim 10, wherein the component B) is dicamba-N,N-bis-(3-aminopropyl)methylamine salt or dicamba-diethylenetriamine salt.

15. The method of claim 10, wherein the component A) and the component B) are the respective N,N-bis-(3-aminopropyl)methylamine salt or diethylenetriamine salt.

16. The method of claim 10, wherein the crop plant is soybean.

17. The method of claim 10, wherein the unwanted vegetation to be controlled is selected from the family of Amaranthaceae.

18. The method of claim 10, wherein the unwanted vegetation to be controlled is selected from the class of Amaranthus.

19. The method of claim 10, wherein the crop plants are tolerant or resistant to component A) and/or component B).

* * * * *